United States Patent [19]
Kobayashi

[11] 3,959,467
[45] May 25, 1976

[54] LIPID METABOLISM IMPROVING AND ANTI-ATHEROMATIC AGENT

[75] Inventor: Mizuho Kobayashi, Gifu, Japan

[73] Assignee: Amano Pharmaceutical Co., Ltd., Nagoya, Japan

[22] Filed: Mar. 11, 1974

[21] Appl. No.: 450,175

Related U.S. Application Data

[60] Division of Ser. No. 329,981, Feb. 6, 1973, Pat. No. 3,875,007, which is a continuation-in-part of Ser. No. 303,312, Nov. 3, 1972, abandoned.

[52] U.S. Cl. .............................................. 424/117
[51] Int. Cl.² ........................................ A61K 35/00
[58] Field of Search ................................... 424/117

*Primary Examiner*—Stanley J. Friedman
*Attorney, Agent, or Firm*—Browdy and Neimark

[57] ABSTRACT

A lipid metabolism improving and anti-atheromatic agent comprises as an active ingredient a new lipolytic substance GA-56 capable of specifically decomposing chylomicron and low-density lipoprotein and having high intestinal absorbability.

9 Claims, 2 Drawing Figures

LIPID METABOLISM IMPROVING AND ANTI-ATHEROMATIC AGENT

CROSS-REFERENCE TO RELATED APPLICATIONS

This is a division of application Ser. No. 329,981 filed Feb. 6, 1973, now Patent No. 3,875,007, which is in turn a continuation-in-part of Ser. No. 303,312 filed Nov. 3, 1972, now abandoned.

BACKGROUND OF THE INVENTION

It is known that the triglyceride taken as food is generally hydrolyzed in intestine and the hydrolyzate is synthesized again to triglyceride as chyromicron in the intestinal wall, from where it moves to the liver via blood and lymph vessels and is then resynthesized to the various lipoproteins. Therefore, various lipoproteins are present in blood while maintaining a suitable concentration relation in the state of normal lipid metabolism. However, once the lipid metabolism becomes abnormal, the various lipoprotein concentrations increase to cause hyper lipemia resulting in various diseases.

It has heretofore been believed that these lipoproteins are decomposed by lipoprotein lipases and that the resulting fatty acids are incorporated in tissues. However, surprisingly, we have found that in rabbits fed with a high chlosterol diet for about six months there results fatty liver and hyper lipemia to high degree; and also the lipoprotein lipase activity was higher than in normal rabbits. Also in patients of hyper lipemia of Types II to IV according to Frederickson's classification of hyper lipemia, it appears that the activity of the lipoprotein lipase is not different from the activity in normal subjects. Thus, the question has existed as to why disorders in lipid metabolism occur even in the absence of an interference with the activity of lipoprotein lipase.

BRIEF SUMMARY OF THE INVENTION

Accordingly we considered that normal lipid metabolism, especially decomposition of lipoproteins, is not only influenced by the lipoprotein lipase released in blood, but that another factor dominates it, and we conducted research to determine what this other factor is. As a result, we have succeeded in confirming the presence of a lipase in liver which is different from the lipoprotein lipase present in plasma, fat tissue or heart muscle. And, it is considered that this lipase acts specifically on chylomicron in the liver to effectively improve lipid metabolism. This hypothesis was demonstrated by the experiment showing that this lipase exhibits an abnormal activity in pathological animals suffering from abnormal lipid metabolism. When a disorder is brought about for some cause, hyper lipemia occurs, which results in more serious diseases such as hyper cholesteremia and fatty liver. In such case, sufficient improvement is not attained only by enhancing the activity of the lipoprotein lipase by administration of heparin or heparinoid. Recently these diseases could be treated only by the control of diet.

This invention relates to a lipid metabolism improving and anti-atheromatic agent comprising a new lipolytic substance having the following properties: (1) it acts specifically on natural fat and oil, chylomicron and low-density-lipoprotein to decompose them, (2) it has an optimum activity at a pH range of from 7 to 11, (3) it has an optimum activity at a temperature of between 40°C and 50°C, (4) it suffers no inactivation in 60 minutes treatment at 37°C and at pH 4, (5) it suffers substantially little inactivation in the presence of inorganic salts, (6) it is completely free of sugar, (7) its molecular weight is approximately 30,000, and (8) its mobility as measured by paper electrophoresis is $1.53 \times 10^{-5}$ cm$^2$, sec$^{-1}$, V$^{-1}$ ( pH = 8.7, $\mu$ (on strength) = 0.05).

DETAILED DESCRIPTION OF THE INVENTION

Figure 1:
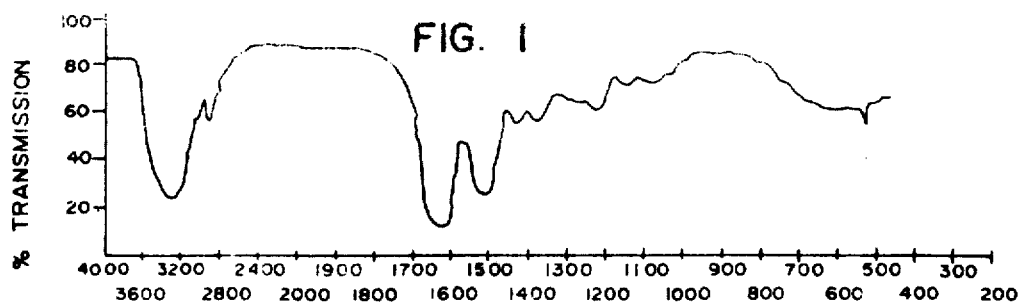

We believed that a new lipolytic substance having a lipase activity like the lipase in liver could be obtained from soil, especially microorganisms, so that when the new lipolytic substance was applied to the treatment of patients of hyper lipemia, the lipid metabolisms could be improved and normal metabolism could be recovered. Thus, we conducted extensive research on various microorganisms and succeeded in collecting a substance meeting the above requirements from bacteria. As a result of detailed examination of physical and chemical properties of this substance, it was confirmed that this substance is a new lipolytic substance which has heretofore been unknown. When this substance was administered to pathological animals suffering from hyper lipemia, it was found that the lipid concentration in blood could apparently be normalized with rapid improvement in lipemia or lipemic plasma turbidity. We gave the name "new lipolytic substance GA-56" to this substance. The new lipolytic substance GA-56 will be referred to merely as "GA-56" hereinbelow.

GA-56 which is an active ingredient of the lipid metabolism improving and anti-atheromatic agent of this invention is a new substance having physiochemical properties quite different from those of known lipases and lipoprotein lipases. Physiochemical properties of GA-56 will now be illustrated while clarifying differences of GA-56 from known lipases and lipoprotein lipases.

1. Function:

GA-56 acts on ester linkages of trigylceride in various lipids and produces fatty acids and glycerine.

2. Substrate Specificity:

A variety of natural fats and oils are utilized as substrates for GA-56. GA-56 decomposes as substrates vegetable oils such as olive oil, sesame oil, rape seed oil and peanut oil, animal oils such as lard and butter, fat and oils activated by albumin or serum protein, and lipoproteins, thereby to produce fatty acids and glycerine.

3. Optimum pH range and stability pH range:

GA-56 acts within a broad pH range of more than 3, and an optimum pH range is on the alkaline side, namely from 7 to 11. When it is treated at 37°C for 60 minutes, no inactivation is caused at a pH value of more than 4.

4. Measurement of Activity:

Twenty ml of 0.1 M phosphate buffer solution (pH = 7) containing 5% of bovine serum albumin (Fraction V, Grade No. of Wako) is mixed with 3 ml of Fatgen (sesame oil emulsion manufactured by Dainippon Seiyaku) to provide a substrate solution. 1.0 ml of the prepared substrate solution and 0.5 ml of 0.1 M phosphate buffer solution (pH = 7) are mixed in a test tube, and they are pre-incubated at 37°C for 5 minutes. Then, diluted GA-56 is added to the tube and incubation is carried out at 37°C for 20 minutes. Then, 5.0 ml of stop solution is added and the mixture is shaken, followed by addition of 3.0 ml of n-heptane and 2.0 ml of distilled water. The mixture is shaken for 10 seconds, and is then allowed to stand still, whereupon it separates into two phases. 3.0 ml of the heptane phase is pipetted by a safety pipette. Indicator solution (1% of thymol blue in alcohol) is added dropwise and nitrogen gas is blown in this solution and titrated with 0.01 N alcoholic potassium hydroxide solution by micropipette. Titration is effected until a slight blue color appears. The blank value is obtained by employing distilled water instead of the diluted GA-56 solution and conducting the above procedures. The stop solution is a liquid mixture comprising 10 parts by volume of n-heptane, 40 parts by volume of isopropyl alcohol and 1 part by volume of 2 N sulfuric acid. The activity of releasing 1 micromole of fatty acid is defined as an activity of one unit.

5. Preferable Temperature for Function of GA-56:

The best function is observed at about 40° to 50°C

6. Inactivating Temperature and pH Conditions:

Inactivation is extreme by the treatment at 37°C for 60 minutes with an acidic liquor having a pH of less than 4. An aqueous solution of GA-56 is 70% inactivated by the treatment at 60°C for 60 minutes.

7. Inhibition, Activation and Stabilization:

GA-56 is not at all inactivated by most inorganic salts, and the activity is increased in a sesame oil emulsion incorporated with albumin or serum protein.

8. Purification Method:

The crude powder of GA-56 obtained from culture broth is dissolved in water of a volume 10 times as great as the powder, and the solution is centrifuged for 10 minutes at 10,000 r.p.m. The supernatant is salted out at a saturation of 0.2 with ammonium sulfate (grade No. 1) and allowed to stand still for about 2 to 3 hours. Then, it is centrifuged again for 10 minutes at 10,000 r.p.m. Then, the precipitate is dissolved in water of a volume 10 times as great as the precipitate. The solution is filtered with Sephadex G-50 gel washed preliminarily with distilled water, and active fractions are mixed together. The mixture is passed through a DEAE-cellulose column bufferized with 0.01 M phosphate buffer solution (pH = 8), and GA-56 is absorbed thereon. The absorbed GA-56 is eluted out by the linear gradient elution method using the above buffer solution contained with sodium chloride where the salt concentration is linearly heightened to 0.5 M. The active fraction is subjected again to the gel filtration with Sephadex G-75, followed by lyophilization to obtain a standard sample of GA-56 exhibiting a single band corresponding to protein activity.

9. Molecular Weight:

GA-56 has a molecular weight of about 30,000 as measured by the gel filtration method.

10. Mobility:

GA-56 has a mobility of $1.53 \times 10^{-5} cm^2$, $sec^{-1}$, $V^{-1}$ as measured by the paper electrophoresis (pH = 8.7, $\mu$ = 0.05).

11. Sugar Content:

GA-56 is negative at the sugar content test method.

12. Crystal Structure:

Since GA-56 is not obtained in the crystal form, purity of the substance was judged by electrophoresis (acrylamide disc electrophoresis method). As a result of the test conducted under conditions of 300V, 2 mA, 60 minutes and pH of 9.4, a single band was obtained which corresponded to protein activity.

Figure 2:
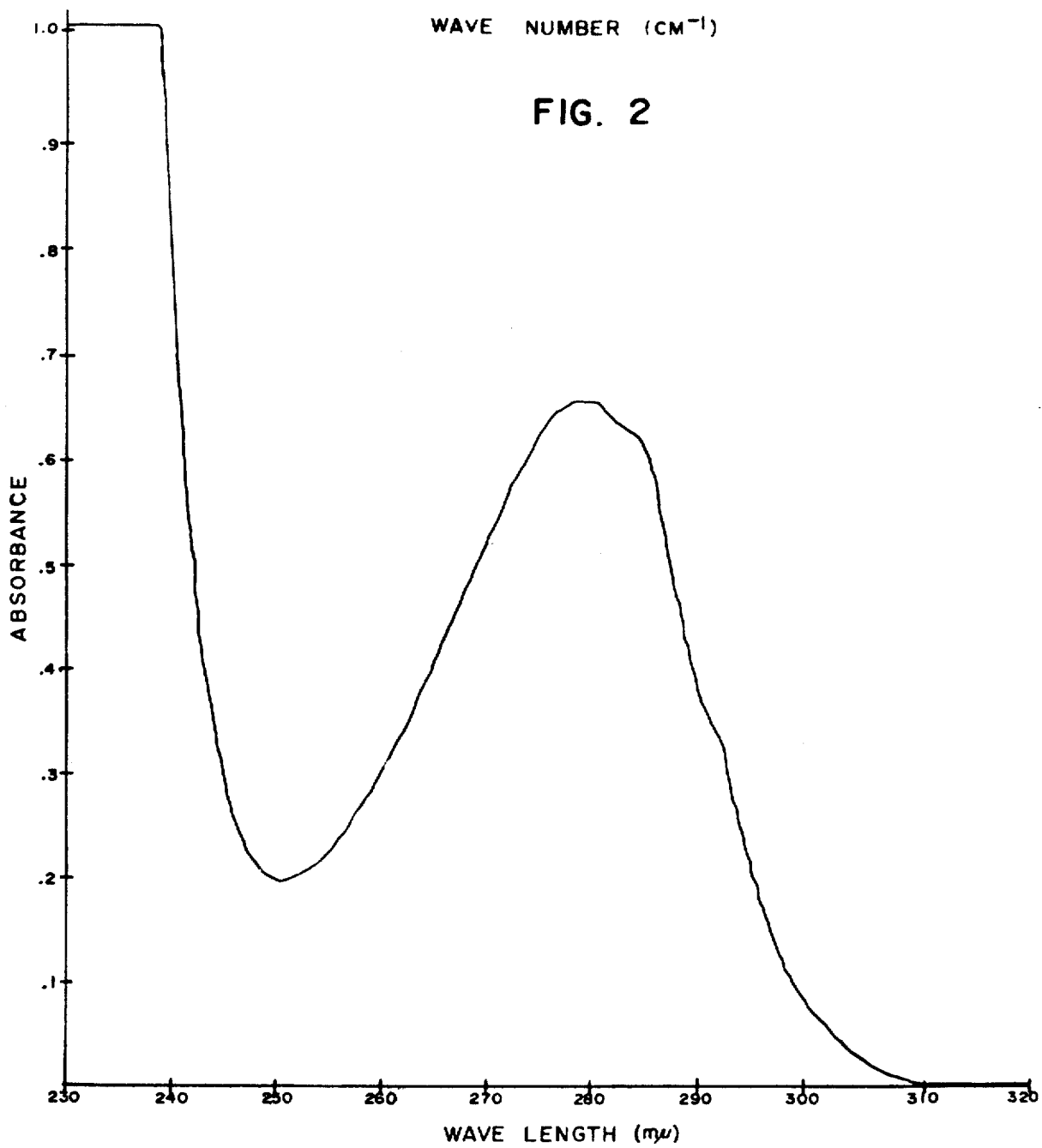

13. its ultra-violet absorption spectrum is as shown in FIG. 1, 14. its infrared absorption spectrum by K Br disk is as shown in FIG. 2, 15. its elementary analysis gives C: 45.72%, H: 6.85%, O: 26.05%, N: 14.38%, S: 0.34%.

No substance having the same physicochemical properties as the above-mentioned properties of GA-56 has been found. Known substances resembling GA-56 are (1) an endogenous lipoprotein lipase observed in blood after intravenous injection of heparin and (2) a lipoprotein lipase microbiologically obtained (U.S. Pat. No. 3,431,175). GA-56 is substantially different from these known substances with respect to function, substrate specificity and the like. Further, it has been proved experimentally that GA-56 is clearly distinguished over the prior substances with respect to heat stability and that GA-56 is quite different from them with respect to influence by inhibitors. Differences between GA-56 and a lipoprotein lipase obtained microbiologically disclosed in U.S. Pat. No. 3,431,175 are shown in Table I below.

TABLE I

| Properties | GA-56 | Lipoprotein Lipase disclosed in U.S. Pat. No. 3,431,175 |
|---|---|---|
| lipolytic activity | decomposition is observed when olive oil emulsion alone is present | decomposition is not observed when olive oil emulsion alone is present |
| influence by inhibitor | not inhibited by sodium chloride, sodium fluoride, protamine sulfate | inhibited with sodium chloride, sodium fluoride, protamine sulfate |
| sugar content | negative | positive |
| electrophoretic mobility ($cm^2$, $sec^{-1}$, $V^{-1}$) | $1.53 \times 10^{-5}$ | $0.70 \times 10^{-5}$ |

As mentioned above, GA-56 of this invention is a new substance which is quite different from known lipoprotein lipases. Further, this new substance has such a remarkable new property that it can readily be absorbed from intestine and thus the possibility of oral administration is suggested. Methods for absorption of high molecular substances such as enzymes from intestine have heretofore been reported by many investigators, but there is no established theory of possibility of intestinal absorption of such substances and the fact is that there are some cases where such substances can be absorbed intestinally only slightly. Anti-inflammatory enzymes such as trypsin and chymotrypsin and proteolytic enzymes of other origins have been tested by the radioactive tracing method, the everted sac method, the intestinal perfusing method, etc. and the possibility of intestinal absorption of such substances is conjectured. However, test conditions have greatly deviated from the living state.

In contrast to these known substances, GA-56 of this invention has such a novel property that when solution containing GA-56 dissolved in water at a certain concentration is injected directly in duodenum of rabbits and rats, the presence of the same substance as administered can be confirmed in peripheral blood.

More specifically, groups of rats (Wister strain; body weight = 250 to 300g; male) each group consisting of 5 rats, were fasted for 24 hours and GA-56, obtained in Example 1 given hereinbelow, was injected into the duodenum of each rat in an amount of 6,000 u/kg. Blood was collected 1 hour after the administration, and serum was separated to determine the activity. The average value of 5 rats of one group was calculated. Results are shown in Table II below. In the group to which GA-56 was administered, the activity was about 10 times the value obtained in the control group. Thus, it can be confirmed that GA-56 can be absorbed directly from intestine.

TABLE II

| Group | Acitivity in Blood ($\mu$/ml) |
|---|---|
| GA-56 administered group 1 | 0.497 |
| GA-56 administered group 2 | 0.400 |
| Control group | 0.042 |

As is seen from the results shown above, it has been confirmed that GA-56 is very specifically absorbed from intestine of rats and the activity can be measured in blood. Further, in order to confirm the activity of GA-56 in blood, heat stability and influence by inhibitors of the serum after administration of GA-56 in duodenum were examined.

Since GA-56 has a very high stability against heat, after administration of GA-56 the serum ws incubated in water bath at 56°C for 30 minutes, under which endogenous lipases, especially blood lipoprotein lipase, are completely inactivated, and the presence of the remaining activity was examined. As a result it was found that while an endogenous lipoprotein lipase was completely inactivated by the heating at 56°C for 30 minutes, the serum collected after duodenum application still retains 76% activity after the same treatment. This value approximates 80% remaining activity obtained in the case of an aqueous solution containing 0.001% of GA-56. Thus it was confirmed that the activity of GA-56 is quite different from that of the endogenous lipoprotein lipase with respect to heat stability and that GA-56 can be absorbed from intestine.

Influences by sodium fluoride, protamine sulfate, sodium chloride and heparin have been reported as differences between lipoprotein lipases and other tissue lipases. Thus, we examined the effects of the above four substances on the serum after intraduodenal administration of GA-56 and on the serum lipoprotein lipase obtained after intravenous injection of heparin. More specifically, (1) GA-56 was administered intraduodenally to a rabbit in an amount of 50,00 u/kg or (2) heparin was intravenously injected in a rabbit in an amount of 20 mg/kg. The above four inhibitors were allowed to act on each of the serum obtained in (1) and the serum obtained in (2) (lipoprotein lipase) at a concentration of 0 to 1.0 M in the case of sodium chloride, 0 to 0.4 M in the case of sodium fluoride, and 0 to 2.0 mg/ml in the case of heparin and protamine sulfate; and the remaining activities were measured.

As a result, it was confirmed that serum (1) and serum (2) exhibited quite different effects against the inhibitors. More specifically, serum (2) was completely inactivated by sodium chloride at a concentration of 0.5 M and sodium fluoride at a concentration of 0.2 M, while serum (1) exhibited remaining activities of 50% and 80%, respectively. Further, serum (1) was not affected by protamine sulfate at 0.5 mg/ml while the activity of serum (2) was found to be reduced to 80% by protamine sulfate at 0.5 mg/ml. Based on these experimental results, it was confirmed that GA-56 has properties quite different from those of endogenous lipoprotein lipases.

Such influences by inhibitors are generally observed in lipoprotein lipases. For instance, the microbial lipoprotein lipase disclosed in U.S. Pat. No. 3,431,175 has similar properties. It was thus confirmed that when GA-56 is duodenally administered, the presence of GA-56 in blood can be proved and that GA-56 is a substance which is quite different from endogenous lipoprotein lipases with respect to influence against various inhibitors. In other words, it was confirmed that activities proved to be manifested in serum obtained after intraduodenal administration of GA-56 cannot be deemed to be due to endogenous lipoprotein lipase but they are exhibited by GA-56 absorbed from intestine.

Further, it was confirmed that GA-56, which can be absorbed from intestine as readily as mentioned above, has such a new specific substrate-decomposing property that, in vivo, experiments, GA-56 has a clearing of highly improving lipemia or lipemic plasma turbidity. More specifically, rats (Wister strain; body weight = 180 to 200 g; male) after fasting for 24 hours were tested. A butter lipemia group of 5 rats were allowed to eat butter freely after fasting, and 3 hours later GA-56 was intramuscularly injected at a dose of 30,000 u/5 ml/kg. A Tween 80 lipemia group of 5 rats were intravenously injected with 400 ml/2 ml/kg of Tween 80 after fasting, and 3 hours later GA-56 was intramuscularly injected at a dose of 30,000 u/5 ml/kg. One hour after injection of GA-56, blood was collected and the lipid concentration in serum was measured. Results are shown in Table III below in which each value is an average value of 5 rats.

TABLE III

| Lipemia | Butter Administered Group | | Tween 80 Administered Group | |
|---|---|---|---|---|
| | Before administration of GA-56 | after administration of GA-56 | Before administration of GA-56 | after administration of GA-56 |
| Turbidity (at O.D. 60) | 0.482 | 0.026 | 0.110 | 0.078 |
| Triglyceride | 810 | 41 | 100 | 28 |

TABLE III-continued

| Lipemia | Butter Administered Group | | Tween 80 Administered Group | |
|---|---|---|---|---|
| | Before administration of GA-56 | after administration of GA-56 | Before administration of GA-56 | after administration of GA-56 |
| (mg/dl) | | | | |

As is seen from the results shown in Table III, in rats of the butter administered group and of the Tween 80 administered group, the triglyceride content in blood was reduced by 90% and 70%, respectively, by administration of GA-56. Thus, it was confirmed that GA-56 exhibits a prominent effect of improving lipemia and is obviously effective for decomposing and clearing lipemia composed mainly of dietetic chylomicron caused by butter administration and lipemia composed mainly of beta-lipoprotein caused by Tween 80 administration. In view of the chemical properties of GA-56, it may readily be conjectured that GA-56 of this invention can act greatly on chylomicron having a high lipid content and the like. It is also considered that it is a property peculiar to GA-56 in vivo that it has a high affinity with lipoprotein brought about by a surface active agent such as Tween 80 (condensation product of ethylene oxide and sorbitan mono-oleate; viscosity 600 to 800cp at 25°C,; density 1.05 to 1.10).

From the above-mentioned experimental results it was confirmed that GA-56 administered into duodenum can be absorbed from the intestinal canal and manifests activities in blood to hydrize the lipoprotein and to clean lipid blood.

As is seen from the above experimental results, GA-56 of this invention is effective for improving hyper lipemia, and, since it can be absorbed from the intestinal canal, even when orally administered, GA-56 is suitable for long-term treatment by continuous administration. Further, it is possible to cure directly hyper lipemia (in blood) by intramuscular or intravenous injection of pure GA-56.

Method of Manufacture of GA-56

Strains No. 156-A and No. 156-B were at first separated from soil as bacteria producing GA-56 of this invention.

Microbiological properties of these two strains will now be detailed. Strains No. 156-A and No. 156-B exhibit properties quite similar to each other and they differ only in very limited properties. Thus, only when the properties differ between these strains, description will be made individually, giving a special reference such as No. 156-A or No. 156-B.

a. Morphology
1. rods: (0.6 to 1.0 $\mu$) × (2.0 to 3.0 $\mu$)
2. single or in pairs and in chains
3. motile with single polar flagellum
4. no spore
5. gram stain: negative
6. acid-fastness: negative b. Cultural Characteristics
1. bouillon agar plate culture; circular growth of entire convex, smooth surface of light grayish brown color, semi-transparent
2. bouillon agar slant culture; filiform growth with smooth entire, moderate degree of growth, circular, yellowish brown, slightly lustrous
3. bouillon liquid culture: moderate growth with thin pellicle on surface, slightly turbid
4. bouillon gelatin stab culture: moderate growth with liquefaction of infundibule form
5. litmus milk: slightly alkaline, litmus-reductive, liquefaction with slight formation of precipitates c. Biological Properties
1. reduction of nitrate: positive (succinic acid-sodium nitrate medium
2. denitrification: negative
3. MR test: positive
4. VR test: negative
5. formation of indole: negative
6. formation of hydrogen sulfide: positive (weak)
7. hydrolysis of starch: negative
8. utilization of citric acid: negative
9. utilization of inorganic nitrogen source: nitrate is not utilized but ammonium salt is utilized
10. pigment formation:
    i. klieglar medium: No. 156-A produces greenish yellow fluorescent pigment (water-soluble) but No. 156-B produces no pigment
    ii. king medium: red (slightly violet) pigment (No. 156-A), negative (No. 156-B)
    iii. tyrosin media: slightly brown pigment (water-soluble)
    iv. glutamic acid-agar medium; faintly yellow, water-soluble pigment
11. ureases: positive
12. oxidase: positive
13. catalase: positive
14. growing pH: 5 9
15. growing temperature:
    10°C  20°C  25°C  30°C  37°C  42°C
    (+)   (++)  (++++) (+++) (−)   (−)
16. attitude to oxygen: aerobic
17. O-F test; oxidative
18. formation of acid and gas from saccharides:
    i. formation of acid; as shown in Table IV below
    ii. formation of gas; negative

Table IV

| Saccharides | Strain No. 156-A | Strain No. 156-B |
|---|---|---|
| L-arabinose | + | + |
| D-xyrose | + | + |
| D-glucose | + | + |
| D-mannose | + | + |
| D-fractose | + | + |
| Maltose | + | + |
| sucrose | + | − |
| lactose | + | + |
| trehalose | + | + |
| D-sorbitol | − | − |
| D-mannitol | + | − |
| inositol | − | − |
| glycerine | + | − |
| starch | − | − |
| D-galactose | + | + |

The above taxological properties were determined according to "Manual of Microbiological Methods" (compiled by the American Society for Microbiology) and "Summary of Microbiological Experiments" (compiled by Infectious Disease Institute, University of Tokyo). When these properties are considered in the system of the key of classification of bacteria in "Bergey's Manual of Determinative Bacteriology", 7th edition, the above two strains are deemed to belong to the genus Pseudomonas, because they are rods with a single polar flagellum, have no function of forming spores and are characterized by having a positive catalase property, and being aerobic. When these properties are examined in detail relying on "Journal of Fermentation", Vol. 49, No. 12, pgs. 968–980 (1971), "Medicinal Journal of Osaka University", Vol. 21, No. 1, pages 1–6 (1970) and "The Journal of General Microbiology", Vol. 43, No. 2, it is considered that these strains resemble Pseudomonas fragi, Pseudomonas cepacia, and Pseudomonas mephitica. However, the above two strains are different from these known strains as shown in Table V below.

Table V

| Test Items | Strain No. 156-A | Strain No. 156-B | Pseudomonas mephitica | Pseudomonas fragi | Pseudomonas cepacia |
|---|---|---|---|---|---|
| Gelatin liquefaction | + | + | + | + | − |
| Litmus milk | liquefaction | liquefaction | liquefaction | solidification | |
| Nitrate reduction | + | + | + | − | − |
| Indole formation | − | − | + | − | − |
| Hydrogen sulfide formation | + | + | + | − | − |
| Growth at pH of 4.5 | − | − | − | | + |
| Growth at 37°C | − | − | + | − | + |
| Formation of acid from saccharides | | | | | |
| D-fractose | + | + | + | − | − |
| maltose | + | + | + | − | + |
| sucrose | + | − | + | − | + |
| D-sorbitol | − | − | + | | + |
| D-mannitol | + | − | + | − | + |
| lactose | + | + | + | − | + |
| inositol | − | − | + | | + |
| glycerine | + | − | + | − | + |

As is seen from the foregoing, taxilogical properties of strains No. 165-A and No. 156-B to be utilized in this invention do not coincide with those of any known strain belonging to the genus Pseudomonas. Further, each of these strains with respect to microbiological properties are very similar. Therefore, it is deemed that these two strains may be included in one species. Accordingly, we have established novel species Pseudomonas nov. sp. No. 156 and both strain No. 156-A and strain No. 156-B have been classified as belonging to the above new species.

In other words, Pseudomonas nov. sp. No. 156 has strain No. 156-A and strain No. 156-B as standard strains and includes varieties and mutants thereof.

Both strains No. 156-A and No. 156-B were deposited with the Fermentation Research Institute, Agency of Industrial Science and Technology, Japan, and they are preserved as FERM-P No. 1431 and FERM-P No. 1432, respectively, at said depository. Furthermore, strains No. 156-A and No. 156-B were deposited with the American Type Culture Collection, Rockville, Md., and deposition numbers ATCC 21,808 and ATCC 21,809 have been allotted to strains No. 156-A and No. 156-B respectively. All restrictions on the availability to the public of these strains will be irrevocably removed upon the granting of the patent and the deposit will be maintained to assure the permanent availability thereof to the public throughut the effective life of the patent resulting from this application.

Ordinary liquid culture and solid culture methods may be utilized for culture of strains No. 156-A and No. 156-B. It is preferred that these strains be cultured in a culture medium which incorporates oil and fat into a fundamental medium comprising glucose, cornsteep liquor, urea, monopotassium hydrogen phosphate, potassium chloride and magnesium sulfate.

As the oil and fat to be incorporated in the above fundamental culture medium, there may be mentioned, for instance, vegetable oils such as olive oil, sesame oil, rape seed oil and peanut oil, soybean oil, rice oil, coconut oil corn oil, castor oil, linseed oil, caco fat, etc., and animal oils such as lard, butter, beef tallow, sheep fat, etc. These oils and fats allow sufficient propagation of the above strains and they play an important role as carbon source for producing GA-56. In general, the amount incorporated of such oil and fat is 0.5 − 2.0% by weight based on the culture medium. The so formed culture media are infected with strains No. 156-A and No. 156-B, and culturing is effected aerobically at 25° − 28°C. In about 24 to 30 hours, production of GA-56 reaches a maximum. Isolation of GA-56 from the resulting culture broth can be accomplished by removing the cells from the culture broth by a centrifugal separator, concentrating the filtrate in vacuo, adding to the concentrate cold ethyl alcohol or acetone in a volume 1 to 3 times the volume of the supernatant, and removing the precipitate by centrifugation, adding to the supernatant ethyl alcohol or acetone of a volume 2 or 3 times the volume of the supernatant, washing the resulting precipitates with 95% ethyl alcohol or acetone and drying them in vacuo at room temperature. Instead of the above-mentioned organic solvent precipitation method, it is posible to adopt, for instance, a method comprising salting out the clear filtrate with ammonium sulfate or other salt, subjecting the resulting precipitate to dialysis so as to remove the salt therefrom, and then lyophylizing.

Formulations of GA-56

GA-56 may be formed into drugs such as tablets, capsules, powders, injections and suppositories. In the case of drugs for oral administration, it is preferred that GA-56 drugs are so formed that they become soluble after they reach the intestines. In the case of injection formulations, GA-56 is used in the highly purified form. In the case of oral drugs or suppositories, GA-56 may be used in the form of crude powder or the roughly purified state, and it is incorporated with an extender, a binder and a suitable base such as cocoa butter and the admixture is molded into tablets, filled in capsules or formed in suppositories. Exterior coatings of known compositions may be used for tablets and capsules for oral administration.

This invention will now be illustrated in more detail by reference to Examples which are offered illustratively.

EXAMPLE 1

Fifteen liters of a liquid culture both (pH - 6) comprising 3% of cornsteep liquor, 1% of glucose, 0.06% of ures, 0.2% of dipotassium hydrogen phosphate, 0.05% of potassium chloride, 0.05% of magnesium sulfate and 1.0% of soybean oil was charged in a jar fermenter of a 30-liter capacity and sterilized at 120°C for 30 minutes in high pressure. Then, the culture broth was infected with 600 ml of a pre-cultured broth obtained by pre-culturing *Pseudomonas nov. sp.* No. 156-A strain at 26°C for 24 hours in a similar culture broth as that defined above. The culture was effected at 26°C, 200 r.p.m. and 0.4 vvm under agitation and passing air through the culture broth. In 24 hours, the production of GA-56 reached a maximum.

After completion of the culturing, the culture broth was centrifuged by means of a centrifugal separator to remove the cells, and the filtrate was concentrated in vacuo at 30°C until the vollume was reduced to one-fifth. Cold ethyl alcohol of a volume 2 times the volume of the concentrate was gradually added to the concentrate under agitation, and the resulting precipitates were filtered by means of a filter press using diatomaceous earth as a filtering assistant. Then, the filtrate was combined under agitation with cold ethyl alcohol of a volme 2.5 times the volume of the filtrate to form of precpitates again. The supernatant liquor was removed, and the remaining precipitates were washed sufficiently with cold ethyl alcohol, centrifuged to remove ethyl alcohol and dried in vacuo at room temperature to give 33 g of white powder of GA-56 having an activity of 58,000 u/g.

EXAMPLE 2

Fifteen liters of a liquid culture broth (pH - 6) containing 3% of cornsteep liquor, 1% of glucose, 0.6% of urea, 0.2% of dipotassium hydrogen phosphate, 0.05% of potassium chloride, 0.05% of magnesium sulfate and 1.5% of olive oil was poured into a jar fermenter of a 30-liter capacity, and sterilized at 120°C for 30 minutes at high pressure. Then, the culture broth was implanted with 600 ml of a pre-cultured broth obtained by pre-culturing *Pseudomonas nov. sp.* No. 156-B strain for 24 hours in a culture broth similar to that described above. The culture was effected at 26°C, 200 r.p.m., and I vvm in an agitated state by passing the air through the culture broth. In 28 hours, the production of GA-56 reached a maximum. After completion of the culture, post-treatments were carried out in the same manner as in Example 1 to obtain 25g of white powder of GA-56 having an activity of 52,000 u/g.

EXAMPLE 3

Fifteen liters of a lquid culture broth (pH = 6) containing 0.6% of urea, 0.2% of dipotassium hydrogen phosphate, 0.05% of potassium chloride, 0.05% of magnesium sulfate and 1.0% of lard was poured into a jar fermenter of a 30-liter capacity, and after sterilization at 120°C for 30 minutes at high pressure it was infected with 600 ml of a pre-cultured broth obtained by pre-culturing *Pseudomonas nov. sp.* No. 156-A strain for 24 hours in a culture broth similar to that described above. The culture was effected at 26°C, 200 r.p.m. and 0.5 vvm in an agitated state by passing the air through the culture broth. In 30 hours, the production of GA-56 reached a maximum. In the same manner as in Example 1, post-treatments were carried out to obtain 40g of white powder of GA-56 having an activity of 54,000 u/g.

EXAMPLE 4

I - Sugar Coated Tablets (Enteric Coated Tablets)
A. Composition (one tablet of 100 mg):

| | | | |
|---|---|---|---|
| (1) | GA-56 | 10,000 $\mu$ | (25%) |
| (2) | synthetic aluminum silicate | 10% | |
| | crystalline cellulose | 3% | |
| | lactose | 3% | |
| (3) | calcium carboxymethyl cellulose | 2.5% | |
| (4) | Hydroxy Propyl Cellulose-SL | 1% | |
| (5) | magnesium stearate | 0.5% | |
| (6) | 9 parts of hydroxypropylmethyl cellulose phthalate and 1 part of diethyl phthalate | 5% | |
| (7) | sugar coating | 50% | |
| (8) | tar pigments | trace | |

B. Preparation Method:

Ingredients (1) to (5) were blended in amounts indicated above, and strip tablets were prepared from the blend according to the tablet method specified in J.P. VIII Pharmaceutical General Rule. An enteric coated film was applied to the so-formed strip tablets with use of the ingredient (6) in an amount indicated above according to the Rule. Then, a sugar coating was applied to the so-filmcoated tablets with use of ingredients (7) and (8) in amounts indicated above according to the sugar coating method specified in J.P. VIII Pharmaceutical General Rule.

C. Method of administration:

One tablet 3 times daily (600 units per Kg of body weight per day), after meals.

II - Drugs for internal Use (Enteric Coated Capsules)
A. Composition (one capsule of 200 mg):

| | | | |
|---|---|---|---|
| (1) | GA-56 powder | 25,000 $\mu$ | (50%) |
| (2) | synthetic aluminum silicate | 30% | |
| | crystalline cellulose | 10% | |
| | lactose | 10% | |

B. Preparation Method:

Ingredients (1) and (2) were blended in amounts indicated above, and prescribed amounts of the blend were filled up into capsules according to the capsule method specified in J.P. VIII Pharmaceutical General Rule. Then, an enteric film was coated on the so-filled capsules according to the filmcoating method specified in J.P. VIII Pharmaceutical General Rule.

C. Method of administrtion:

One capsule 1 time daily (500 units per Kg of body weight per day), after meal.

III - Drugs for Internal Use (Suppositories)
A. Composition (one suppository of 200 mg):

| | | |
|---|---|---|
| (1) | GA-56 | 25,000 $\mu$ |
| (2) | one part of methyl paraben and one part of butyl paraben | trace |
| (3) | cacao or suitable suppository base | suitable amount |

B. Preparation Method:

From the above ingredients were prepared suppositories according to the suppository method specified in J.P. VIII Pharmaceutical General Rule.

C. Method of administration:

One suppository daily (500 units per Kg of body weight per day).

Administration Test (Enteric Coated Tablets)

Rabbits (body weight - 2.5 kg; male) were intravenously injected with 200 mg/kg of Triton WR 1339 to form a lipemia. Twenty-two hours later, enteric coated tablets were forcibly administered orally to the rabbits at a dose of 10,000 u/kg of body weight.

Five ml of blood was collected from ear vein at every prescribed period, and serum was separated therefrom to determine the triglyceride content in serum and the activity of GA-56. Results are shown in Table VI below. As is seen from these results, in the control group even after 6 hours, the content of the endogenous lipid in blood, i.e., triglyceride, was as high as 94% of the triglyceride content observed 22 hours after injection of Triton WR 1339. On the other hand, in the GA-56 administered group, in 2 hours, the lipid content was already reduced, and in 6 hours, the lipid content was reduced by about 35%. This coincides with the fact that in the control group hardly any change was observed in the activity in blood, while in the GA-56 administered group, in 4 – 6 hours, the activity was almost tripled.

Table VI

| Time (hours) | Triglyceride Content (mg/dl) | | Activity ($\mu$/ml) | |
|---|---|---|---|---|
| | control group | GA-56 administered group | control group | GA-56 administered group |
| 0 | 485 | 455 | 0.07 | 0.06 |
| 2 | 470 | 390 | 0.06 | 0.10 |
| 4 | 480 | 320 | 0.06 | 0.18 |
| 6 | 457 | 294 | 0.05 | 0.17 |

In view of the foregoing, it can be judged that GA-56 has an ability to decompose prominently endogenous lipids and is very effective for improvement of the lipid metabolism.

EXAMPLE 5

Drugs for Internal Use (Capsules with Enteric Coated Granules)

A. Composition (one capsule of 400 mg):

| (1) | GA-56 | 10,000 $\mu$ (25%) |
|---|---|---|
| (2) | synthetic aluminum silicate | 32% |
| | crystalline cellulose | 10% |
| | lactose | 11% |
| (3) | calcium carboxymethyl cellulose | 10% |
| (4) | Hydroxy Propyl Cellulose-SL | 2% |
| (5) | 9 parts of hydroxypropylmethyl cellulose phthalate and 1 part of diethyl phthalate | 10% |
| (6) | tar pigments | trace |

B. Preparation Method:

Ingredients (1) to (4) were blended in amounts indicated above, and the blend was molded into globular granules (15 to 50 mesh) according to the granule method specified in J.P. VIII Pharmaceutical General Rule. Then, the granules were coated with an enteric film with use of ingredients (5) and (6) of amounts indicated above according to the film coating method specified in J.P. VIII Pharmaceutical General Rule. Then, prescribed amounts of the enteric film-coated granules were filled up into capsules.

C. Method of administration:

One capsule 3 times daily (600 units per Kg of body weight), after meals.

ADMINISTRATION TEST

Three groups of rabbits (body weight = 2.5 kg; male), each group consisting of 5 rabbits, were fed with 100g of 1% cholesterol diet per day. In one group (group II), the drug prepared in this example was given together with the cholesterol diet. In another group (group III), after the cholesterol feeding was continued for 8 weeks, administration of the drug obtained in this Example was started. In the control group (group I), the cholesterol feeding was effected without administration of the drug obtained in this Example. In this manner, the cholesterol diet feeding was continued for 22 weeks in each group. The administration of the drug (capsule) was effected once every day forcibly orally at a dose of 10,000 u/kg as calculated as active ingredient GA-56.

In each group, the abdominal incision was conducted under general anesthesia, and aorta arcus was removed. This tissue was fixed with formalin, and frozen sections having a thickness of 15$\mu$ were sliced therefrom. Then, after staining with Sudan-IV these preparates were examined hystochemically by high power microscope.

As a result, it was found that in the rabbits of group I, the obvious atherosclerotic picture was observed in both of the inner layer and the middle layer. In 40% of the rabbits of group II, no lipid deposition was observed and in the remaining 60%, slight lipid deposition was observed in the inner layer. In each of the rabbits of group III, lipid deposition was observed in the inner layer, and when the degree of the deposition was compared by extraction of the lipid, it was found that the degree of the lipid deposition in Group III was only 20 to 30% of the deposition degree in the control group I. It was also found that in the tissue preparation obtained from the rabbits administered with the capsule of GA-56 there was formed a tissue picture deemed to be due to the effect of GA-56 in amelioration against the formation of atheromatics.

EXAMPLE 6

Drug for Internal Use (Injection)

A. Composition (one vial):

| (1) | purified GA-56 | 50 $\mu$ |
|---|---|---|
| (2) | dissolving liquor (isotonic sodium chloride solution) | 2 ml |

Purified GA-56 was dissolved in the dissolving liquor when injection was effected.

B. Preparation Method:

The purified GA-56 (exhibiting a single band at the disc electrophoresis) was aseptically filled in a prescribed amount according to J.P. VIII Pharmaceutical General Rule to obtain a lyophilized ampule. The dissolving liquor was prepared by dissolving sodium chloride in injectional sterile distilled water, filtering the solution, filling the filtrate into ampules and effecting the sterilization at 115°C for 30 minutes.

C. Method of administration:

One vial daily (1 unit per Kg of body weight per day).

Administration Test

Triton WR 1339 was injected intravenously in an amount of 200 mg/kg of body weight into rabbits (body weight = 2.5 kg; male) to form a lipemia. After 22 hours, one ampule of the purified GA-56 sample was dissolved in 2 ml of sterilized physiological saline and intravenous injection was conducted at a dose of 10 u/kg of body weight.

Five ml of blood was collected from an ear vein at every prescribed period, and serum was separated to determine the triglyceride conccentration in serum and the activity. As a result, it was found that the triglyceride concentration in blood tended to increase in 4 hours in the control group, whereas reduction of about 30% in the triglyceride concentration was observed in the GA-56 administered group. Thus, as in Example 4 it was confirmed that GA-56 is effective for improving the lipid metabolism. Results obtained in this Example are shown in Table VII below.

TABLE VII

| Time (hours) | Triglyceride Concentration (mg/dl) | | Activity in Blood ($\mu$/ml) | |
|---|---|---|---|---|
| | control group | GA-56 administered group | control group | GA-56 administered group |
| 0 | 437 | 441 | 0.05 | 0.06 |
| 2 | 437 | 353 | 0.07 | 0.15 |
| 4 | 479 | 303 | 0.07 | 0.11 |

Having thus described my invention the following claims set forth that which is to be secured by Letters Patent of the United States.

I claim:

1. A composition for reducing the content of endogenous lipid in the blood of patients having hyperlipemia or for ameliorating atherosclerosis in patients having atherosclerosis comprising an effective amount of lipolytic substance GA-56, and a pharmacutically acceptable carrier, said lipolytic substance GA-56 having the following characteristics: (1) its acts specifically on natural fat and oil, chylomicron and low-density lipoprotein to decompose them, (2) optimum pH range is from 7 to 11, (3) optimum temperature is between 40° and 50°C, (4) it suffers no inactivation in 60 minute treatment at 37°C and a pH 4, (5) it suffers substantially little inactivation in the presence of inorganic salts, (6) it is completely free of sugar, (7) its molecular weight is approximately 30,000, (8) its mobility as measured by paper electrophoresis is $1.53 \times 10^{-5}$ cm$^2$, sec$^{-1}$, v$^{-1}$ (pH=8.7, $\mu$ = 0.05), (9) its ultra-violet absorption spectrum is as shown in FIG. 2, (10) its infrared absorption spectrum is as shown in FIG. 1, and (11) its elementary analysis gives C: 45.72%, H: 6.85%, O: 26.05%, N: 14.38%, S: 0.34%

2. A composition in accordance with claim 1 wherein said carrier is a pharmaceutically acceptable diluent.

3. A composition in accordance with claim 1 wherein said carrier is a pharmaceutically acceptable injection medium.

4. A composition in accordance with claim 1 wherein said carrier is a pharmaceutically acceptable suppository diluent.

5. A method for reducing the content of endogenous lipid in the blood of patients having hyperlipemia, comprising administering to said patient lipolytic substance GA-56 in an effective amount sufficient to reduce the content of endogenous lipid in the blood, said lipolytic substance GA-56 having the following characteristics: (1) its acts specifically on natural fat and oil, chylomicron and low-density lipoprotein to decompose them, (2) optimum pH range is from 7 to 11, (3) optimum temperature is between 40° and 50°C, (4) it suffers no inactivation in 60-minute treatment at 37°C and at pH 4, (5) it suffers substantially little inactivation in the presence of inorganic salts, (6) it is completely free of sugar, (7) its molecular weight is approximately 30,000, (8) its mobility as measured by paper electrophoreis is $1.53 \times 10^{-5}$ cm$^2$, sec$^{-1}$, v$^{-1}$ (pH=8.7, $\mu$ 0.05), (9) its ultra-violet absorption spectrum is as shown in FIG. 2, (10) its infrared absorption spectrum is as shown in FIG. 1, and (11) its elementary analysis gives C: 45.72%, H: 6.85%, O 26.05%, N: 14.38%, S: 0.35%.

6. A method in accordance with claim 5 wherein said composition is administered orally.

7. A method in accordance with claim 5 wherein said composition is administered by injection.

8. A method in accordance with claim 5 wherein said composition is adminstered through the rectum.

9. A method for ameliorating atherosclerosis in patients have atherosclerosis, comprising administering to said patient lipolytic substance GA-56 in an effective amount sufficient to ameliorate atherosclerosis, said lipolytic substance GA-56 having the following characteristics: (1) it acts specifically on natural fat and oil, chylomicron and low-density lipoprotein to decompose them, (2) optimum pH range is from 7 to 11, (3 ) optimum temperature is between 40° and 50°C, (4) it suffers no inactivation in 60-minute treatment at 37°C and at pH 4, (5) it suffers substantially little inactivation in the presence of inorganic salts, (6) it is completely free of sugar, (7) its molecular weight is approximately 30,000, (8) its mobility as measured by paper electrophoresis is $1.53 \times 10^{-5}$ cm$^2$, sec$^{-1}$, v$^{-1}$ (pH=8.7, $\mu$ = 0.05), (9) its ultra-violet absorption spectrum is as shown in FIG. 2, (10) its infrared absorption spectrum is as shown in FIG. 1, and (11) its elementary analysis gives C: 47.72% H: 6.85%, O: 26.05%, N: 14.38%, S: 0.35%.

* * * * *